United States Patent
Shimada et al.

(10) Patent No.: US 7,998,693 B2
(45) Date of Patent: Aug. 16, 2011

(54) GENE SPECIFIC TO CANCER AND DIAGNOSIS KIT USING THE SAME

(75) Inventors: Hideaki Shimada, Chiba (JP); Takeshi Tomonaga, Chiba (JP); Kazuyuki Matsushita, Chiba (JP); Takenori Ochiai, Chiba (JP); Fumio Nomura, Chiba (JP)

(73) Assignee: National University Corporation Chiba University (JP)

( * ) Notice: Subject to any disclaimer, the term of this patent is extended or adjusted under 35 U.S.C. 154(b) by 992 days.

(21) Appl. No.: 11/794,798

(22) PCT Filed: Jan. 5, 2006

(86) PCT No.: PCT/JP2006/300242
§ 371 (c)(1),
(2), (4) Date: Jul. 3, 2007

(87) PCT Pub. No.: WO2006/080192
PCT Pub. Date: Aug. 3, 2006

(65) Prior Publication Data
US 2010/0196928 A1      Aug. 5, 2010

(30) Foreign Application Priority Data

Jan. 5, 2005   (JP) ............................... P2005-001033

(51) Int. Cl.
*G01N 1/00* (2006.01)
*G01N 33/53* (2006.01)
(52) U.S. Cl. ............ 435/7.21; 435/2; 435/7.1; 436/501; 436/518; 436/522; 422/50; 530/300; 530/350; 424/130.1
(58) Field of Classification Search .......... None
See application file for complete search history.

(56) References Cited

U.S. PATENT DOCUMENTS

2004/0137434 A1    7/2004 Tang et al.

FOREIGN PATENT DOCUMENTS

| JP | H07-051065 | 2/1995 |
| WO | 02059260 A2 | 8/2002 |
| WO | WO 03/104426 A2 | 12/2003 |
| WO | WO 2004/018679 | 3/2004 |

OTHER PUBLICATIONS

Sugata et al. (Human Molecular Genetics, vol. 9, No. 19, pp. 2919-2926).*
Takeshi Tomonaga et al, Centromere Protein H is Up-regulated in Primary Human Colorectal Cancer and its Overexpression Induces Aneuploidy, Cancer Res., Jun. 2005, p. 4683-p. 4689, vol. 65, No. 1 1, AACR.
Naoko Sugata et al, Characterization of a Novel Kinetochore Protein, CENP-H, The Journal of Biological Chemistry, Jun. 1999, p. 27343-p. 27346, vol. 274, No. 39, The American Society for Biocheimstry and Molecular Biology, Inc., U.S.A.
Naoko Sugata et al, Human CENP-H Multimers Colocalize With CENP-A and CENP-C at Active Centromere-kinetochore Complexes, Human Molecular Genetics, Aug. 2000, p. 2919-2926, vol. 9, No. 19, Oxford University Press.
Takeshi Tomonaga et al., "Overexpression of Centromere Proteins Frequently Observed in Human Primary Colorectal Cancers Induces Aneuploidy Through an Aberrant Localization", Proceedings of the American Association for Cancer Research Annual Meeting, Apr. 2005, p. 1282, vol. 46.
Genbank; Assession No. NM-022909.

* cited by examiner

*Primary Examiner* — Lisa Cook
(74) *Attorney, Agent, or Firm* — Lerner, David, Littenberg, Krumholz & Mentlik, LLP

(57) ABSTRACT

The present invention provides a new additional identification of a gene related to cancer expression and a diagnostic kit using the same.

1 Claim, 3 Drawing Sheets

SEQUENCE LISTING

<160> NUMBER OF SEQ ID NOS: 4

<210> SEQ ID NO 1
<211> LENGTH: 744
<212> TYPE: DNA
<213> ORGANISM: Homo sapiens

<400> SEQUENCE: 1

```
atggaggagc agccccagat gcaagacgcc gacgagcccg cggactccgg aggggaaggc      60
cgggcaggcg ggccaccgca ggtcgccggc gcccaggcgg cgtgcagcga ggaccgcatg     120
accctgctcc tcaggctgag agcacagaca aaacaacaac tcttagaata taaatcaatg     180
gttgatgcaa gtgaagaaaa aactccagaa caaattatgc aagaaaagca aatcgaagct     240
aaaattgaag acctggaaaa tgaaattgaa gaggtaaaag ttgctttga gataaaaaag      300
cttgcattag acaggatgag actttcaact gcacttaaaa aaaacctgga gaaaattagc     360
agacagtcta gtgtgctcat ggataacatg aaacacctat tagagctaaa taaattaata     420
atgaaatcac agcaggaatc ttgggattta gaggaaaaac tgcttgatat tagaaagaag     480
agattgcaat taaaacaagc ttcagaaagt aagcttttag aaatacagac tgaaaagaac     540
aaacagaaga ttgatttgga cagtatggaa aactcagaga ggataaagat catacgacaa     600
aacctacaga tggagataaa aattactact gttattcaac atgtgttcca gaaccttatt     660
ttggggagta aagtcaattg ggcagaggat cctgcccta aggaaattgt tctgcagctt      720
gagaagaatg ttgacatgat gtaa                                             744
```

<210> SEQ ID NO 2
<211> LENGTH: 247
<212> TYPE: PRT
<213> ORGANISM: Homo sapiens

<400> SEQUENCE: 2

```
Met Glu Glu Gln Pro Gln Met Gln Asp Ala Asp Glu Pro Ala Asp Ser
1               5                   10                  15
Gly Gly Glu Gly Arg Ala Gly Gly Pro Pro Gln Val Ala Gly Ala Gln
            20                  25                  30
Ala Ala Cys Ser Glu Asp Arg Met Thr Leu Leu Leu Arg Leu Arg Ala
        35                  40                  45
Gln Thr Lys Gln Gln Leu Leu Glu Tyr Lys Ser Met Val Asp Ala Ser
    50                  55                  60
Glu Glu Lys Thr Pro Glu Gln Ile Met Gln Glu Lys Gln Ile Glu Ala
65                  70                  75                  80
Lys Ile Glu Asp Leu Glu Asn Glu Ile Glu Glu Val Lys Val Ala Phe
                85                  90                  95
Glu Ile Lys Lys Leu Ala Leu Asp Arg Met Arg Leu Ser Thr Ala Leu
            100                 105                 110
Lys Lys Asn Leu Glu Lys Ile Ser Arg Gln Ser Ser Val Leu Met Asp
```

```
                    115                 120                 125
Asn Met Lys His Leu Leu Glu Leu Asn Lys Leu Ile Met Lys Ser Gln
    130                 135                 140

Gln Glu Ser Trp Asp Leu Glu Glu Lys Leu Leu Asp Ile Arg Lys Lys
145                 150                 155                 160

Arg Leu Gln Leu Lys Gln Ala Ser Glu Ser Lys Leu Leu Glu Ile Gln
                165                 170                 175

Thr Glu Lys Asn Lys Gln Lys Ile Asp Leu Asp Ser Met Glu Asn Ser
                180                 185                 190

Glu Arg Ile Lys Ile Ile Arg Gln Asn Leu Gln Met Glu Ile Lys Ile
                195                 200                 205

Thr Thr Val Ile Gln His Val Phe Gln Asn Leu Ile Leu Gly Ser Lys
    210                 215                 220

Val Asn Trp Ala Glu Asp Pro Ala Leu Lys Glu Ile Val Leu Gln Leu
225                 230                 235                 240

Glu Lys Asn Val Asp Met Met
                245

<210> SEQ ID NO 3
<211> LENGTH: 21
<212> TYPE: DNA
<213> ORGANISM: Homo sapiens

<400> SEQUENCE: 3
cagtctagtg tgctcatgga t                                          21

<210> SEQ ID NO 4
<211> LENGTH: 20
<212> TYPE: DNA
<213> ORGANISM: Homo sapiens

<400> SEQUENCE: 4
tccatctgta ggttttgtcg                                            20
```

GENE SPECIFIC TO CANCER AND DIAGNOSIS KIT USING THE SAME

CROSS REFERENCE TO RELATED APPLICATIONS

This application claims priority under 35 U.S.C. 119 based upon Japanese Patent Application Serial No. 2005-001033, filed on Jan. 5, 2005. The entire disclosure of the aforesaid application is incorporated herein by reference.

FIELD OF THE INVENTION

The present invention relates to a cancer-specific gene and a diagnostic kit using the same, and further relates to a method for using the diagnostic kit.

BACKGROUND OF THE INVENTION

The most crucial challenge in measures against cancer is the early detection of cancer. Particularly, early detection is important for cancers originating from the upper part of the large intestine since they cause only limited subjective symptoms and the medical condition may likely to be in its advanced stage by the time of discovery.

Traditional measures against large intestine cancer include screening by the fecal occult blood test, diagnosis by serum markers such as CEA or CA19-9, and diagnosis during a course of treatment. However, the positive rates of these methods are high only for advanced cancers and extremely low for early cancers, making accurate diagnosis difficult in their early stages.

Meanwhile, a biological diagnostic method using a cancer tissue-specific protein marker is suggested as a method allowing simple and reliable early diagnosis of malignancy. This method can be performed on a broad range of asymptomatic subjects since it does not require a large-scale facility and causes small burdens for the subject. For instance, Japanese Patent Application Publication No. H07-51065 discloses a usage of glycoprotein 39 as a tumor marker.

In addition, International Patent Application Publication No. WO/2004/018679 describes a technology regarding a cancer diagnostic kit using CENP-A. Sugata, N., et al., "Human CENP-H multimers colocalize with CENP-A and CENP-C at active centromere-kinetochore complexes," *Hum. Mol. Genet.*, vol. 9, no. 19, 2000, pp. 2919-2926 discloses the sequences of human CENP-H protein and its corresponding encoding nucleotide which correspond to SEQ ID No: 1 and SEQ ID No: 2 of the present application. Sugata et al. also discloses the biochemical characterization and the localization of CENP-H protein suggesting its role in cell cycle progression.

WO 03/104426 discloses CENP-E with additional background information relating to CENP-A, B, C, and D. Also, WO 03/104426 discloses a method to detect the abnormal amount of CENP-E protein in biopsied tissue for diagnosis of predisposition or actual clinical symptoms of cancer and the kits for detecting the presence of aberrant CENP-E protein expression.

However, cancer expression cannot be thoroughly verified by the technology described in the above JP-A-H7-51065 alone and a plurality of means must be used to ensure positive identifications.

Considering the above situation, the purpose of the present invention is to provide a further identification of a gene related to cancer expression and a diagnostic kit using the same.

SUMMARY OF THE INVENTION

Considering the above situation, the present invention employs specific means described below.

A first means is a polynucleotide as in one of the following (a)-(c):
(a) a polynucleotide consisting of a base sequence as in SEQ ID NO: 1 or a complementary base sequence thereof; (b) a polynucleotide consisting of a base sequence having at least 70% homology with the base sequence as in SEQ ID NO: 1 or the complementary base sequence thereof; and (c) a polynucleotide coding a protein consisting of an amino-acid sequence as in SEQ ID NO: 2, or another amino-acid sequence defined by the amino-acid sequence having one or several amino acid deletions, substitutions or additions, wherein the polynucleotide is a marker for detecting cancer.

The polynucleotide in this means may greatly contribute to a cancer diagnosis when used as a marker since the polynucleotide has been discovered to exhibit a high expression in cancer tissues. The homology with the base sequence as in SEQ ID NO: 1 is preferably equal to or greater than 70%, more preferably equal to or greater than 80%, and even more preferably equal to or greater than 90%.

A second means is a cancer diagnostic kit comprising a primer consisting of a base sequence as in SEQ ID NO: 3.

A third means is a cancer diagnostic kit comprising a primer consisting of a base sequence as in SEQ ID NO: 4.

A fourth means is a cancer diagnostic kit comprising a primer set consisting of the primers as in SEQ ID NOS: 3 and 4. Each of these cancer diagnostic kits may be used to diagnose rectal cancer or colon cancer.

A fifth means is a method comprising the steps of: measuring an expression level of a protein consisting of an amino-acid sequence as in SEQ ID NO: 2 for each of two collected cells; and determining whether or not the ratio between the measured expression levels is equal to or great than 1.7. In this case, one of the two samples is collected from a non-cancer tissue; the other sample is collected from, for example, a tissue suspected to be a cancer tissue; and if the expression level ratios of the two samples are different, the subject from whom the samples were collected may be determined to be at a high risk of cancer.

Preferably for this means, the step of measuring the expression level of the protein is performed with the western blot, wherein one of the two collected cells is a cell in a non-cancer tissue, wherein one of the two collected cells is a cell in a cancer tissue.

As described above, a gene related to cancer expression may be newly identified, and a diagnostic kit using the same may be provided.

DETAILED DESCRIPTION OF THE PREFERRED EMBODIMENTS

Figure 1:
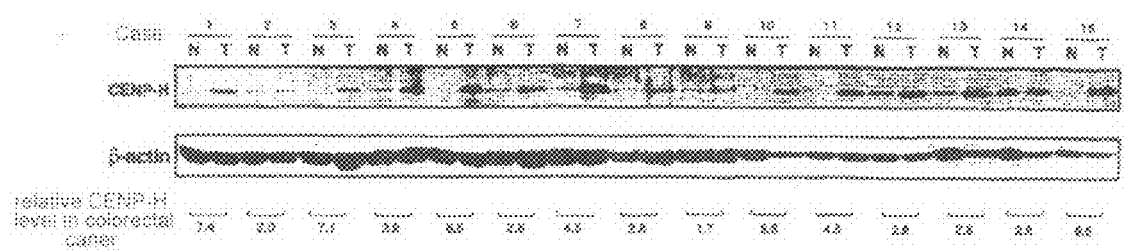
FIG. 1 is a diagram showing western blot results for CENP-H.

One embodiment of the present invention will be described below.

Tissue Collection

Body tissues were collected with a surgical method from 15 patients with early-stage colorectal cancer. The tissues were taken from cancer tissue (hereinafter referred to as "cancer tissue") and tissue at a part 5-10 cm away from the cancer tissue (hereinafter referred to as "non-cancer tissue"), respectively. The collected tissues were immersed in liquid nitrogen and stored at −80° C.

Protein Extraction

The cryonically-preserved tissues were then placed into lysis buffer (7 M urea, 2 M thiourea, 2% 3-[(3-Cholamidopropyl)Dimethylammonio]-1-Propanesulfonate, 0.1 M DTT, 2% IPG buffer (made by Amersham Pharmacia Biotech), 40 mM Tris), lysed using polytron homogenizer (made by Kinematica), and centrifuged at 10,000 g and 4° C. for 1 hour to collect supernatant and extract proteins.

Immunoblot

The proteins were blotted to polyvinylidene fluoride membranes (made by Millipore) in a tank transfer device (made by Bio-Rad) and the membranes were then blocked with phosphate buffered saline (PBS) containing 5% skim milk. Next, 1:5000 diluted rabbit anti-CENP-H antibody, 1:100 diluted rabbit anti-hMis12 antibody and 1:500 diluted goat anti-β-actin antibody, each placed in the blocking buffer, were used as a primary antibody; and 1:3000 diluted goat anti-rabbit IgG HRP and 1:500 diluted rabbit anti-goat IgG HRP, each placed in the blocking buffer, were used as a secondary antibody.

Note that antibodies on the antigen membrane were detected with enhanced chemiluminescence detection reagent (made by Amersham Pharmacia Biotech). Also the intensity of each band was measured with an NIH image.

PCR and Real-Time Quantitative PCR

TotalRNA was extracted from the cancer tissue and the non-cancer tissue, respectively, using RNeasy Mini Kit (made by Qiagen). Also cDNA was synthesized from each extracted totalRNA, respectively, using a 1st Strand cDNA Synthesis Kit for RT-PCR (made by Roche).

Then each cDNA obtained by this synthesis was used as a template to amplify the cDNA of CEMP-H with PCR. In the PCR, a primer comprising a base sequence as in SEQ ID NO: 3 or 4 were used as the forward and reverse primer, respectively, and cDNA of GAPDH or β-actin were amplified as the controls.

Subsequently cDNA real-time quantitative PCR for CENP-H was performed in a LIGHTCYCLER®capillary. For the PCR reaction mixture, 3.0 mM of $MgCl_2$, 0.5 µM of the primer as in SEQ ID NO: 3 and 0.5 µM of the primer as in SEQ ID NO: 4 were added to LIGHTCYCLER® DNA Master SYBR Green I (FastStart Taq DNA polymerase, dNTP, buffer, SYBR Green I), and the procedure was conducted within a total of 2.0 µl.

LIGHTCYCLER® software version 3.3 (made by Roche) was then used for analysis.

Immunohistochemical Staining Method

The frozen tissue sections were dried on a glass slide and fixed in 4° C. acetone. The tissues were then washed with PBS 3 times and blocked with the blocking buffer (10% fetal bovine serum/PBS) for 1 hour.

The sample was incubated for 1 hour in 3% bovine serum albumin/PBS using one or both of 1:2000 diluted rabbit anti-CENP-H antibody and 1:1000 diluted anti-human CENP-A monoclonal antibody. After washing with PBS, the sample was incubated for 1 hour with 1:1000 diluted ALEXA FLUOR® 488- or 594-bound goat anti-rabbit anti-mouse IgG secondary antibody (made by Molecular Probes) and/or ALEXA FLUOR® 594-bound goat anti-mouse IgG secondary antibody.

DNAs were counterstained using DAPI III Counterstain (made by Vysis). The sample was observed with a fluorescence microscope (made by Leica QFISH). The tissue sections were stained with hematoxylin for 30 minutes for HE staining, dried over 100% ethanol and xylene and encapsulated with Permount.

Results

Figure 2:
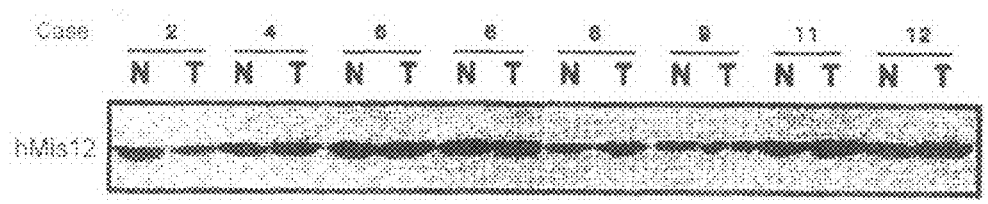
FIG. 2 is a diagram showing western blot results for hMis12.

FIG. 1 shows results of the western blot. As shown in FIG. 1, CENP-H was highly expressed in the cancer tissue in any of the 15 cases. Particularly, a ratio between the non-cancer tissue and the cancer tissue CENP-H expressions was 1.7-9.6, indicating a large difference between these two kinds of tissues. For another centromere protein hMis12, on the other hand, no notable difference was discovered between the cancer tissue and the non-cancer tissue. (See FIG. 2, in which tissues with the same case number as in FIG. 1 are identical with those in FIG. 1).

Figure 3:
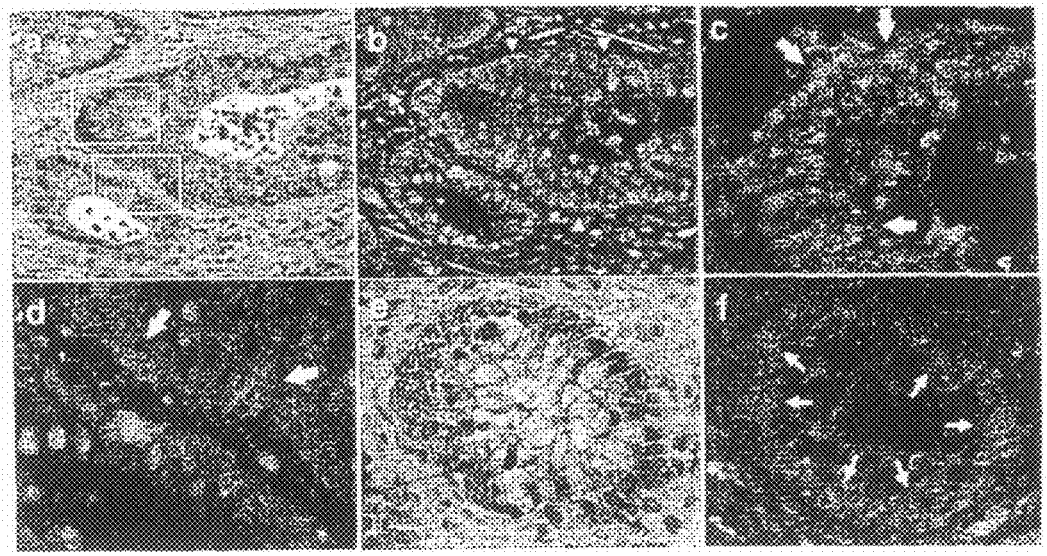
FIG. 3 is a diagram showing the results of staining cross-sectional areas of rectal cancer tissues and their respective nearby non-rectal cancer tissues with anti-human CENP-H polyclonal antibody.

Next, in order to verify that CENP-H is expressed in the cancer cell, but not in stromal cells, cross-sectional areas of colorectal cancer tissues and nearby non-cancer tissues were stained with an anti-human CENP-H polyclonal antibody. The results are shown in FIG. 3. Note that FIG. 3(a) shows an HE-stained image of the cancer tissue; FIGS. 3(b), (c) and (d) show a CENP-H antibody immunostained image of the cancer tissue; FIG. 3(e) shows an HE-stained image of the non-cancer tissue; and FIG. 3(f) shows a CENP-H-stained image of the non-cancer tissue.

As a result, it was confirmed that CENP-H existed as small patchy points in cell nuclei at positions coinciding with the centromeres in a similar manner to that of other centromere proteins such as CENP-A and CENP-C. It was also confirmed that the CENP-H had been increased both in number and size in the cancer tissues (FIGS. 3(c) and (d)) compared to the non-cancer tissue (FIG. 3(f)). It should be noted that the stained CENP-H was verified not in the stromal cells, but in the cancer tissue epithelia. Also the present experiment was conducted on various tissue sections and all the results were similar to each other.

Accordingly, it was confirmed that CENP-H was expressed in cancer cells.

Subsequently, in order to verify that the CENP-H overexpression was a result of its increase due to transcription, amounts of mRNA of CENP-H in the colorectal cancer tissues and the non-cancer tissues were analyzed, respectively, using RT-PCR and real-time quantitative PCR. The results are shown in FIGS. 4 and 5.

Figure 4:
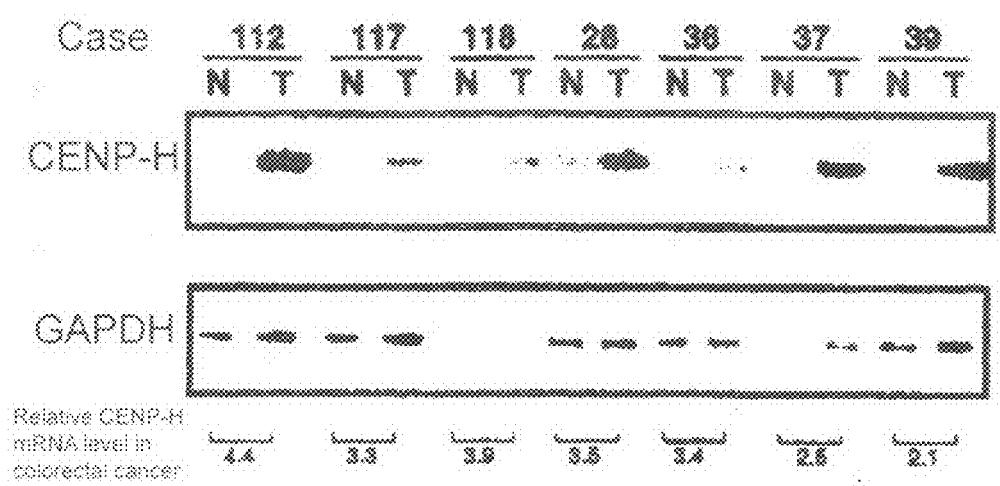
FIG. 4 is a diagram showing analysis results on amounts of CENP-H mRNA in each of the surfaces of rectal cancer tissues and normal tissues using RT-PCR and real-time quantitative PCR.

As shown in FIG. 4, an expression level of the CENP-H mRNA in the cancer tissues is far more increased than in the non-cancer tissues. Furthermore, it was discovered that the expression level of the CENP-H mRNA indicated a strong correlation with the CENP-H expression ratio between the non-cancer tissues and the cancer tissues illustrated in FIG. 1.

As a control, when confirmation was done pertaining to GAPDH, there was no significant difference in the expression level of the CENP-H mRNA between the cancer tissues and the non-cancer tissues.

Figure 5:
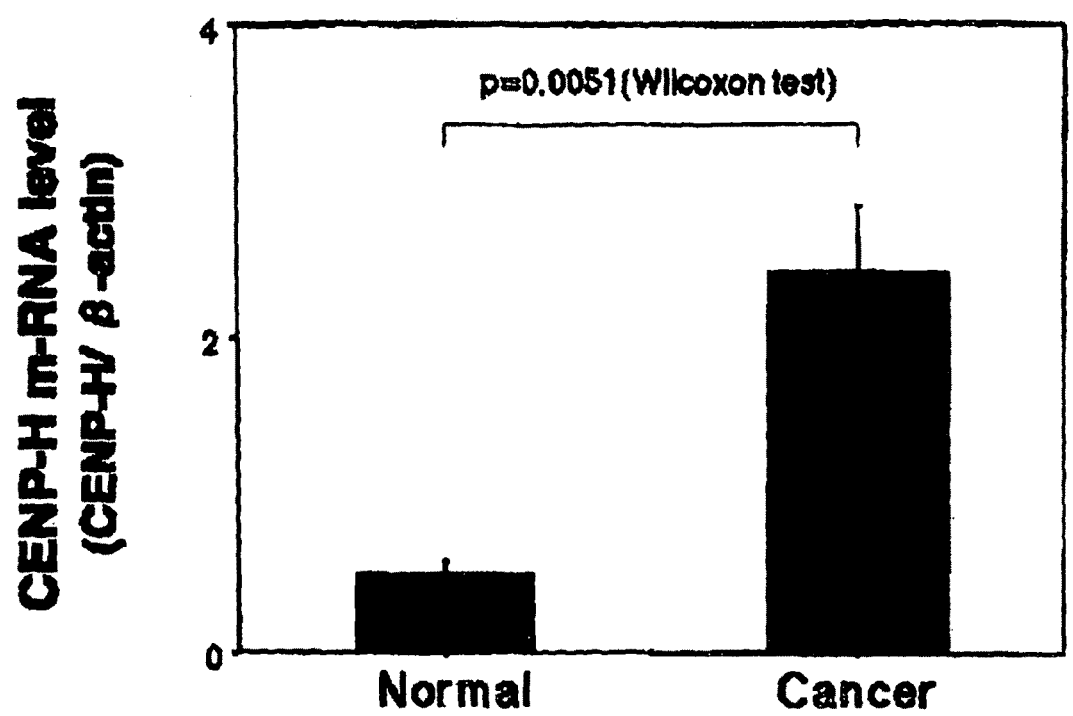
FIG. 5 is a diagram showing analysis results on amounts of CENP-H mRNA in each of the surfaces of rectal cancer tissues and normal tissues using RT-PCR and real-time quantitative PCR.

FIG. 5 illustrates a comparison of the mRNA expression levels shown in FIG. 4 between the non-cancer tissues and the cancer tissues using StatView statistical analysis software. According to FIG. 5, the CENP-H mRNA expression level in the cancer tissues (Cancer) was 5 times higher than that of the non-cancer tissues (Normal). In this way, the presence of cancer can be also verified by examining the CENP-H expression level.

INDUSTRIAL AVAILABILITY

Thus according to the present invention, a gene related to cancer expression may be newly identified, and a diagnostic kit using the same may be also provided.

What is claimed is:

1. A method for detecting rectal cancer or colon cancer, comprising the steps of: measuring an expression level of a protein consisting of an amino-acid sequence as in SEQ ID NO: 2 for each of two collected cells, wherein one of said two collected cells is a cell from a non-cancer tissue and the other of said two collected cells is a cell from a tissue suspected to be a cancer tissue, and wherein said measuring is performed comprising using western blot analysis and using an antibody against the protein consisting of the amino-acid sequence as in SEQ ID NO: 2;
calculating a ratio between the measured expression levels; and
determining the other cell is a rectal cancer or colon cancer cell if the ratio between the measured expression levels is equal to or greater than 1.7.

* * * * *